US 7,390,925 B2

United States Patent
Wu et al.

(10) Patent No.: US 7,390,925 B2
(45) Date of Patent: Jun. 24, 2008

(54) OXIME-CONTAINING ACYL GUANIDINES AS BETA-SECRETASE INHIBITORS

(75) Inventors: Yong-Jin Wu, Madison, CT (US); Samuel Gerritz, Guilford, CT (US); Shuhao Shi, Madison, CT (US); Shirong Zhu, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/693,026

(22) Filed: Mar. 29, 2007

(65) Prior Publication Data

US 2007/0232581 A1    Oct. 4, 2007

Related U.S. Application Data

(60) Provisional application No. 60/788,799, filed on Apr. 3, 2006.

(51) Int. Cl.
C07C 233/05    (2006.01)
A61K 31/65    (2006.01)

(52) U.S. Cl. .................. 564/164; 564/157; 564/165; 514/616; 514/619

(58) Field of Classification Search ............... 564/157, 564/164, 165; 514/616, 619
See application file for complete search history.

(56) References Cited

U.S. PATENT DOCUMENTS 7,049,344 B2 * 5/2006 Magdolen et al. .......... 514/619
2002/0099083 A1 * 7/2002 Schelberger et al. ....... 514/384

FOREIGN PATENT DOCUMENTS

WO    WO 92/14697    9/1992

OTHER PUBLICATIONS

Hussain, I. et al., "Identification of a Novel Aspartic Protease (Asp 2) as β-Secretase", *Mol. Cell. Neurosci*, (1999) 14: 419-427.
Lin, X. et al., "Human aspartic protease memapsin 2 cleaves the β-secretase site of β-amyloid precursor protein", Proceedings of the National Academy of Sciences of the USA, (2000) 97: 1456-1460.
Luo, Y., et al., "Mice deficient in BACE1, the Alzheimer's β-secretase, have normal phenotype and abolished β-amyloid generation", *Nature Neuroscience* (2001) 4: 231-232.
Roberds, S.L. et al.,"BACE knockout mice are healthy despite lacking the primary β-secretase activity in brain: implications for Alzheimer's disease therapeutics", *Human Molecular Genetics* (2001) 10: 1317-1324.

Seiffert, D.; et al., "Presenilin-1 and -2 are molecular targets for γ-secretase inhibitors", *J. Biol. Chem.* (2000) 275, 34086-34091.
Selkoe, D. J., "Alzheimer's Disease: Genes, Proteins, and Therapy", *Physiol. Rev.* (2001) 81, 741-766.
Selkoe, D. J., "Biochemical Analyses of Alzheimer's Brain Lesions lead to the Identification of αβ and its Precursor", *Ann. Rev. Cell Biol.* (1994) 10: 373-403.
Sinha, S., et al., "Purification and cloning of amyloid precursor protein β-secretase from human brain", *Nature* (London) (1999) 402: 537-540.
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.
Walsh, D. M., et al., "Naturally secreted oligomers of amyloid β protein potently inhibit hippocampal long-term potentiation in vivo", *Nature* (2002) 416, 535-539.
Wolfe, M. S., "Secretase Targets for Alzheimer's Disease: Identification and Therapeutic Potential", *J. Med. Chem.* (2001) 44, 2039-2060.
Yan, R. et al., "Membrane-anchored aspartyl protease with Alzheimer's disease β-secretase activity", *Nature* (1999) 402: 533-537.

* cited by examiner

*Primary Examiner*—Shailendra Kumar
(74) *Attorney, Agent, or Firm*—Aldo A. Algieri

(57) ABSTRACT

There is provided a series of substituted oxime-containing acyl guanidines of Formula (I)

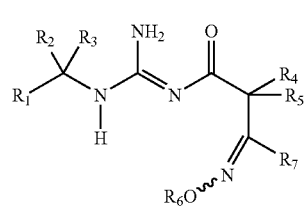

or a stereoisomer; or a nontoxic pharmaceutically acceptable salt thereof, wherein $R_1$, $R_2$, $R_3$, $R_4$, $R_5$, $R_6$, and $R_7$ are as defined herein, their pharmaceutical compositions and methods of use. These compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

9 Claims, No Drawings

OXIME-CONTAINING ACYL GUANIDINES AS BETA-SECRETASE INHIBITORS

CROSS-REFERENCE TO RELATED APPLICATIONS

This is a non-provisional application which claims the benefit of U.S. Provisional Application No. 60/788,799 filed Apr. 3, 2006.

FIELD OF THE DISCLOSURE

This patent application provides substituted oxime-containing acyl guanidines having drug and bio-affecting properties, their pharmaceutical compositions and method of use. In particular, the disclosure is concerned with a series of oxime-containing acyl guanidines which are inhibitors of β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.,* 1994, 10: 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., (1999) *Mol. Cell. Neurosci.,* 14: 419-427; Lin, X. et al., (2000) *Proceedings of the National Academy of Sciences of the United States of America,* 97: 1456-1460; Sinha, S., et al., (1999) *Nature (London),* 402: 537-540; Vassar, R., et al., (1999) *Science (Washington, D.C.),* 286: 735-741; Walsh, D. M. et al., (2002); Wolfe, M. S. (2001); Yan, R. et al., (1999) *Nature (London),* 402: 533-537].

Removal of BACE activity in mice by gene targeting completely abolishes Aβ production [see Luo, Y., et al., (2001) *Nature Neuroscience,* 4: 231-232; Roberds, S. L. et al., (2001) *Human Molecular Genetics,* 10: 1317-1324].

BACE –/– mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publications WO 92/14697, published Sep. 3, 1992, discloses substituted guanidines and derivatives thereof as modulators of neurotransmitter release.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of oxime-containing acyl guanidine derivatives having the Formula (I)

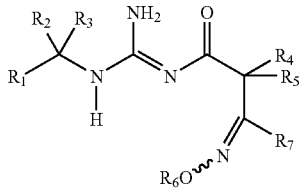

or a stereoisomer; or a nontoxic pharmaceutically acceptable salt thereof, wherein $R_1$, $R_2$, $R_3$, $R_4$, $R_5$, $R_6$, and $R_7$ as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

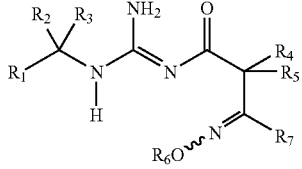

wherein
$R_1$ is phenyl optionally substituted with one or more groups selected from halogen, CN, $CF_3$, OH, $-NH_2$, $C_{3-6}$cycloalkyl, $C_{1-6}$alkoxy, $C_{2-6}$alkenyl, $C_{1-6}$alkyl optionally substituted with OH or $-NH_2$, $-(CH_2)_m-NHC(=O)OC_{1-6}$ alkyl, $-(CH_2)_m-NHC(=O)O$phenyl optionally substituted with halogen; $-(CH_2)_m-NHC(=O)R_8$ and $-NHC(=O)R_9$;

$R_2$ and $R_3$ are each independently hydrogen, methyl or trifluoromethyl;

m is 0 or 1;

$R_4$ and $R_5$ are each independently hydrogen or fluoro;

$R_6$ is hydrogen, $C_{1-6}$alkyl, trifluoromethyl or $C_{3-6}$cycloalkyl;

$R_7$ is phenyl or indol-3-yl optionally substituted with one or more groups selected from halogen, CN, $CF_3$, $OCH_3$, $NO_2$, $NH_2$, and $NHC(=O)C_{1-6}$alkyl;

$R_8$ is $C_{1-6}$alkyl or $C_{3-6}$cycloalkyl in which each is optionally substituted with a group selected from halogen, CN, $CF_3$ and $C_{1-4}$alkoxy;

$R_9$ is $-C_{1-6}$alkyl$NR_{10}R_{11}$;

$R_{10}$ is hydrogen or $C_{1-6}$alkyl;

$R_{11}$ is hydrogen, $C_{1-6}$alkyl optionally substituted with OH, halogen, $C_{1-4}$alkoxy or $C_{1-4}$alkylcarboxyl; $-(CH_2)_mC_{3-6}$ cycloalkyl optionally substituted with phenyl or $C_{1-4}$alkyl; $-(CH_2)_m$phenyl optionally substituted with halogen, hydroxyl or $C_{1-4}$alkoxy; or $R_{10}$ and $R_{11}$ together with the nitrogen to which they are attached is azetidine, aziridine, pyrrolidine, piperidine or homopiperidine in which each is optionally substituted with a group selected from halogen, $C_{1-6}$alkyl and $C_{1-4}$alkoxy;

or a nontoxic pharmaceutically acceptable salt thereof.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Colin Dingwall, *Journal of Clinical Investigation*, Nov. 2001, 108 (9): 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, 3-methylbutyl, hexyl and the like. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of "$C_{1-6}$ alkoxy" include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. It is understood, that whether a chiral center in an isomer is "R" or "S" depends on the chemical nature of the substituents of the chiral center. All configurations of compounds of the invention are considered part of the invention. Additionally, the carbon atom to which $R_2$ and $R_3$ is attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "nontoxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional nontoxic salts or the quaternary ammonium salts of the parent compound formed, for example, from nontoxic inorganic or organic acids. For example, such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Reaction Scheme 1 describes a general synthesis of compounds of formula I. Beta-ketoesters of formula 1, wherein $R_8$ is methyl or ethyl, can be converted to oximes of formula 2 through treatment with a compound of formula $R_6ONH_2$.HCl salt in a polar solvent such as ethanol at 80° C. The hydrolysis of esters of formula 2 can be carried out under basic conditions such as aqueous lithium hydroxide in THF at room temperature to provide acids of formula 3. The coupling reaction of acids of formula 3 with amines of formula 4 can be effected using a coupling reagent in the presence of a base. The preferred coupling reagent is benzotriazol-1-yloxytripyrrolidinophosphonium hexafluorophosphate, and the preferred base is triethylamine. Compounds of formula 5 can be converted to those of formula 7 upon treatment with amines of formula 6 in a solvent such as THF or dichloromethane. Treatment of compounds of formula 7 with a acid such as trifluoroacetic acid (TFA) can remove the BOC protecting group and provide compounds of formula I.

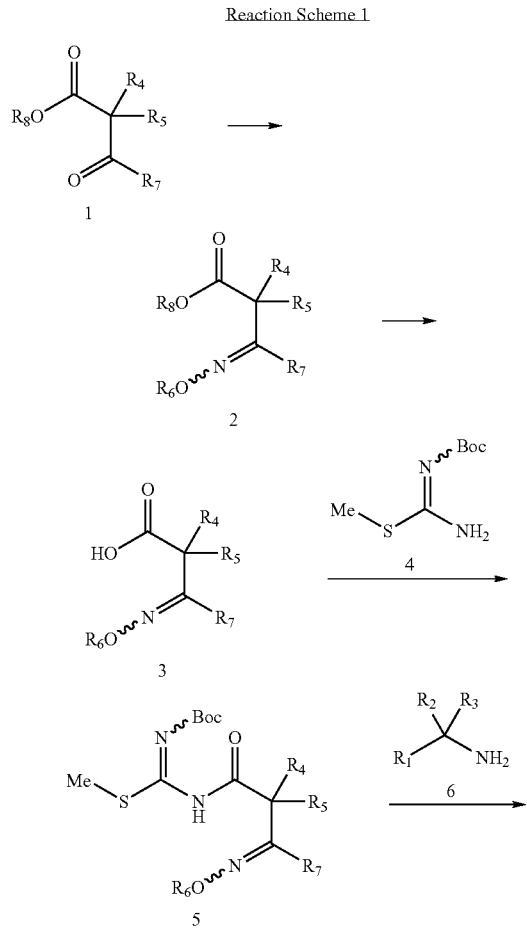

Reaction Scheme 1

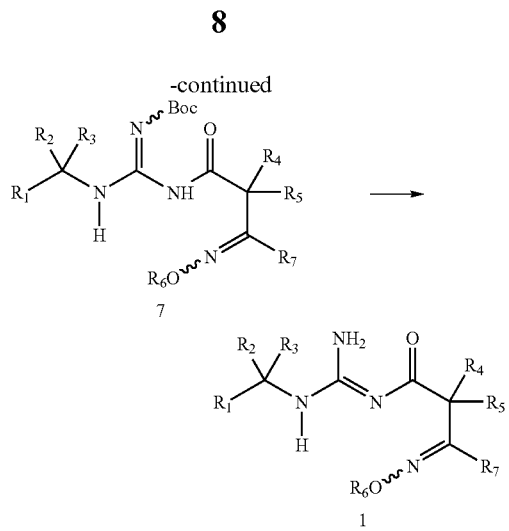

Reaction Scheme 2 describes an alternative synthesis of compounds of formula 7. Treatment of intermediate of formula 4 with compounds of formula 6 can produce compounds of formula 8, which can be coupled with acids of formula 3 using benzotriazol-1-yloxytripyrrolidinophosphonium hexafluorophosphate and triethylamine to give compounds of formula 7.

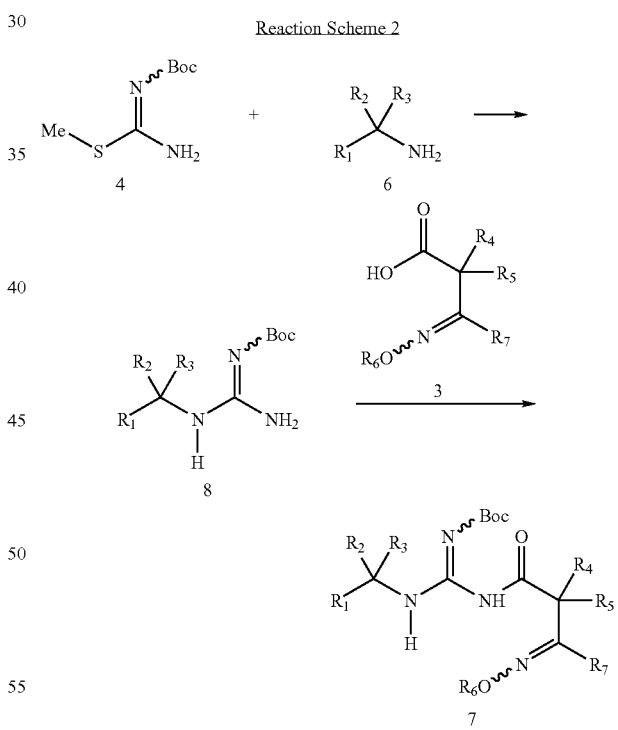

Reaction Scheme 2

Compounds of formula Ia are prepared as illustrated in Reaction Scheme 3. Intermediates of formula 5 (Reaction Scheme 1) are treated with amines of formula 9 to afford compounds of formula 10. Amines of formula 9 can be obtained commercially, or prepared by methods known in the literature, or made by one skilled in the art. Compounds of formula 10 are treated with bromides of formula 11 in the presence of a base such as triethylamine to furnish compounds of formula 12. Bromides of formula 11 can be obtained commercially, or prepared by methods known in the literature, or made by one skilled in the art. Compounds of formula 12 are treated with amines of formula 13 to provide compounds of formula 14, which are converted to compounds of formula Ia under acidic conditions. The preferred acidic conditions include trifluoroacetic acid and hydrochloric acid.

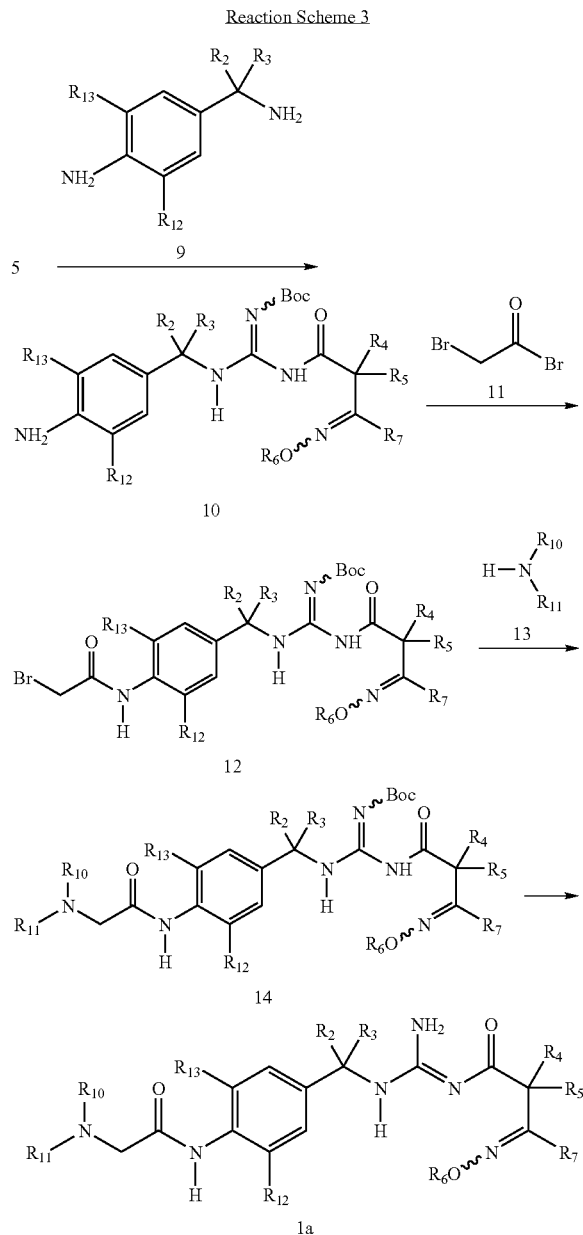

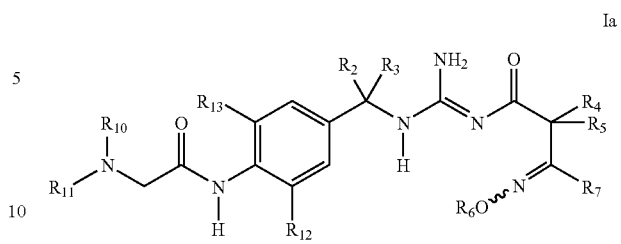

wherein $R_{10}$ is hydrogen or $C_{1-4}$alkyl; $R_{11}$ is hydrogen, $C_{1-4}$alkyl, trifluoromethyl or $C_{4-6}$cycloalkyl; or $R_{10}$ and $R_{11}$ together with the nitrogen to which they are attached is azetidine, aziridine, pyrrolidine, piperidine or homopiperidine; $R_{12}$ and $R_{13}$ are each independently selected from hydrogen, halogen, $C_{1-4}$alkyl and trifluoromethyl; or a nontoxic pharmaceutically acceptable salt thereof.

In a further embodiment, this invention includes pharmaceutical compositions comprising at least one compound of Formula I in combination with a pharmaceutical adjuvant, carrier or diluent.

In another further embodiment, this invention relates to a method of treatment or prevention of disorders responsive to the inhibition of β-amyloid peptide in a mammal in need thereof, which comprises administering to said mammal a therapeutically effective amount of a compound of Formula I or a nontoxic pharmaceutically acceptable salt.

In yet another further embodiment, this invention relates to a method for treating Alzheimer's Disease, cerebral amyloid angiopathy and Down's Syndrome in a mammal in need thereof, which comprises administering to said mammal a therapeutically effective amount of a compound of Formula I or a non-toxic pharmaceutically acceptable salt.

DESCRIPTION OF THE SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δTMS=0. The following internal references were used for the residual protons in the following solvents: $CDCl_3$ ($\delta_H$ 7.26), $CD_3OD$ ($\delta_H$ 3.30) and DMSO-$d_6$ ($\delta_H$ 2.50). Standard acronyms were employed to describe the multiplicity patterns: s (singlet), d (doublet), t (triplet), q (quartet), m (multiplet), b (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method A is as follows unless otherwise noted: Column Phenomenex Luna C18 S10

In a preferred embodiment of the invention $R_2$, $R_3$ and $R_4$ are hydrogen and $R_6$ is preferably methyl or ethyl. It is also preferred that $R_7$ is p-methylphenyl or indol-3-yl.

In another preferred embodiment $R_1$ is 3,6-dichlophenyl, 4-amino-3,6-dichlorophenyl, 4-acetamido-3,5-dichlorophenyl or 4-acetamido-3-methyl-5-chlorophenyl.

In yet another preferred embodiment the compounds of the invention have the formula 1a, (4.6×50 mm), Start % B=0. Final % B=100, Gradient Time=2 min, Flow rate 5 ml/min. Wavelength=220 nm, Solvent A=10% MeOH-90% H₂O -0.1% TFA, Solvent B=90% MeOH-10% H₂O-0.1% TFA; and R$_t$ in min. HPLC method B is the same as method A with the exception of 4 mL/min flow rate. Preparative reverse phase HPLC was performed on a Shimadzu LC-8A automated preparative HPLC system with detector (SPD-10AV UV-VIS) wavelength and solvent systems (A and B) the same as above except where otherwise noted.

The compounds of this application and their preparation can be understood further by the following working examples. These examples are meant to be illustrative of the present application, and are not to be taken as limiting thereof.

Chemical abbreviations used in the specification and Examples are defined as follows:

"Boc" or "BOC" for t-butyloxycarbonyl,
"BOP" for benzotriazol-1-yloxytris-(dimethylamino)-phosphonium hexafluorophosphate,
"CD₃OD" for deuteromethanol,
"CDCl₃" for deuterochloroform,
"DCC" for 1,3-dicyclohexylcarbodiimide,
"DCM" for dichloromethane
"DEAD" for diethyl azodicarboxylate,
"DIEA", "Hunig's base", or "DIPEA" for N,N-diisopropylethylamine,
"DMF" for N,N-dimethylformamide,
"DMAP" for 4-dimethylaminopyridine,
"DMPU" for 1,3-dimethyl-3,4,5,6-tetrahydro-2(1H)-pyrimidone,
"DMSO" for dimethylsulfoxide,
"DPPA" for diphenylphosphorylazide
"EDAC" for 1-(3-dimethylaminopropyl)-3-ethylcarbodiimide,
"Et" for ethyl,
"EtOAC" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"HMPA" for hexamethylphosphoramide,
"LDA" for lithium diisopropylamide,
"LiHMDS" for lithium bis(trimethylsilyl)amide,
"NaHMDS" for sodium bis(trimethylsilyl)amide,
"NMM" for 4-methylmorpholine,
"PyBOP" for benzotriazole-1-yl-oxy-tris-pyrrolidino-phosphonium hexafluorophosphate,
"TMSCH₂N₂" for (trimethylsilyl)diazomethane,
"TMSN₃" for Azidotrimethylsilane,
"TBTU" for O-(1H-benzotriazol-1-yl)-N,N,N',N'-tetramethyluronium tetrafluoroborate,
"TEA" for triethylamine,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

SYNTHESIS OF INTERMEDIATES

Intermediate A 3,5-Dichloro-4-aminobenzylamine

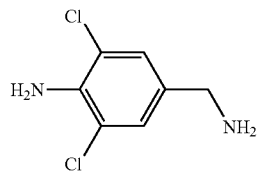

To lithium aluminum hydride (0.57 g, 15 mmol) in dry THF (20 mL) was added dropwise 3,5-dichloro-4-aminobenzonitrile (1.87 g, 10 mmol) in THF (30 mL). The mixture was stirred at rt for 2 h. Then, sodium sulfate decahydrate (4.83 g, 15 mmol) was added and the mixture was stirred for 30 min. The solid was filtered off and washed with THF three times. The solvent was removed under vacuum and the residue was purified by chromatography with Methanol/DCM (3:7) as the eluant. 3,5-Dichloro-4-aminobenzylamine was obtained as an off-white solid (1.5 g, 80%). ¹H NMR (300 MHz, CD₃OD): δ3.65 (s, 2H), 7.2 (s, 2H).

Intermediate B

4-Acetamido-3,5-dichloro-benzylamine

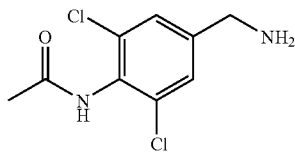

Step B (1): To a solution of 3,5-dichloro-4-amino-benzonitrile (187 mg, 1 mmol) in 4 mL of THF at room temperature was added 2.2 mL of 1.0 M NaHMDS in THF. The resulting reaction mixture was stirred at room temperature for 30 min, at which time acetyl chloride (3.1 mmol) was added. DCM (100 mL) and water (100 mL) were added to the reaction mixture after being stirred overnight, followed by the addition of 5 mL of a 1.4 N HCl aqueous solution. The layers were separated and the aqueous layer was extracted with DCM (2×100 mL). The extracts were combined and solvents were evaporated in vacuo. The residue was purified by HPLC to give 4-acetamido-3,5-dichloro-benzonitrile. MS (ESI) (M–H)⁺=227.05. ¹H-NMR (300 MHz, CDCl₃) δ 7.63 (s, 2 H), 2.21 (s, 3 H).

Step B (2): To a solution of 4-acetamido-3,5-dichloro-benzonitrile (114 mg, 0.5 mmol) in 5 mL of THF was added lithium aluminum hydride (120 mg, 3.2 mmol) in one portion and the resulting mixture was stirred for 3 h. Sodium sulfate decahydrate (1 g, 3.2 mmol) was added in one portion and the mixture was stirred for 30 min. The solid was filtered off and the filtrate was concentrated. The residue was purified by HPLC to give 4-acetamido-3,5-dichloro-benzylamine (35 mg, 30%). ¹H NMR (500 MHz, CD₃OD): δ 7.46 (s, 2 H), 3.78 (s, 2H), 2.18 (s, 3 H).

Intermediate C

N-Boc-S-methylisothiourea

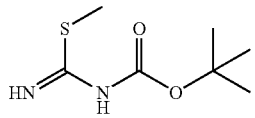

To a rapidly stirred suspension of S-Methylisothiourea hemisulfate (60.8 g, 0.437 mol) in $CH_2Cl_2$ (600 mL) was added 2N NaOH (300 mL, 0.6 mol). This mixture was cooled to 0° C. on an ice bath, and a solution of di-tert-butyl dicarbonate (43.2 g, 0.198 mol) was added dropwise over 6 h. Upon completion of the addition, the mixture was stirred an additional 20 min, diluted with 1 L of $CH_2Cl_2$ and the phases were separated. The organic portion was washed with water (2×500 ml) and dried over $Na_2SO_4$. Filtration and concentration provided the desired N-Boc-S-methylisothiourea as a white solid (35.5 g, 0.187 mol, 94% yield based on $Boc_2O$).

Intermediate D

(Z)-tert-Butyl (4-acetamido-3,5-dichlorobenzylamino)(amino)-methylenecarbamate

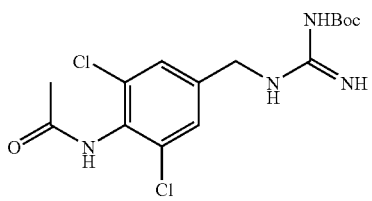

To a solution of mono-N-Boc-S-methylisothiourea (Preparation C, 764 mg, 4.0 mmol) and DIPEA (3.0 mL) in $CH_2Cl_2$ (8.0 mL) was added trifluoroacetic anhydride (924 mg, 4.4 mmol). The mixture was stirred at rt for 30 min, and then N-(4-(aminomethyl)-2,6-dichlorophenyl)acetamide (930 mg, 4.0 mmol) was added. The resulting mixture was stirred at rt overnight. The solvent was removed. Then 15 mL of MeOH and $K_2CO_3$ (1.2 g) were added. After stirring at rt for 30 min, the MeOH was removed. 50 mL of HCl (1 N) was added, and the mixture was washed with $Et_2O$ (50 mL) and then neutralized with 50% NaOH to pH=12. The aqueous layer was then extracted with EtOAc (2×100 mL). The organic layer was dried and concentrated to give 1.1 g (yield 73%) of the title compound. MS (ESI) $(M+H)^+$=375.06. $^1H$ NMR (500 MHz, $CD_3OD$) δ 7.39 (s, 2 H), 4.41 (s, 2 H), 2.19 (s, 3 H), 1.45 (s, 9 H).

Intermediate E

(E)-tert-Butyl (4-amino-3,5-dichlorobenzylamino (amino)methylenecarbamate

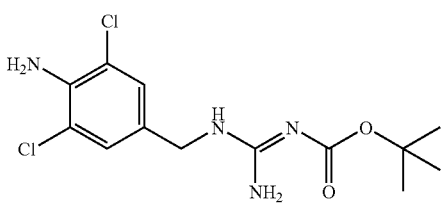

A mixture of 4-(aminomethyl)-2,6-dichlorobenzenamine (150 mg, 0.785 mmol), tert-butyl amino(methylthio)methylenecarbamate (157 mg, 0.825 mmol) and p-toluenesulfonic acid (142 mg, 0.825 mmol) in dichloromethane (4 mL) was stirred at rt for 2 days. The reaction mixture was concentrated under vacuum and purified by filtering through QAX anion exchange cartridge with methanol to provide the title compound as an off-white solid (260 mg, quantitative yield). $^1H$ NMR (400 MHz, $CD_3OD$) δ 1.453 (9H, s), 4.249 (2H, s), 7.162 (2H, s). HPLC retention time: 2.332 min (method A). MS (ESI) $(M+H)^+$ 333.02.

Intermediate F

N-(4-(Aminomethyl)-2,6-dichlorophenyl)-2-(dimethylamino)acetamide

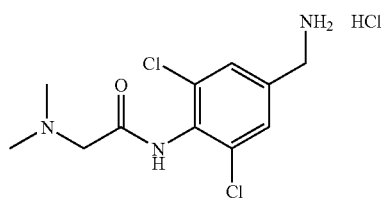

Step F (1): To a solution of intermediate A (9 g, 0.047 mol) in dry THF under $N_2$, diisopropyl ethylamine (8.2 ml, 0.047 mol) was added. The reaction mixture was cooled to 0° C. and then Boc anhydride (10.26 g, 0.047 mol) dissolved in dry THF (25 mL) was added drop wise maintaining the reaction temperature at 0° C. After the addition was over, the reaction mixture was allowed to reach room temperature and stirred for about 2 hrs. After ensuring the absence of the starting material, THF was removed under the vacuum and the resulting solid was dissolved in ethyl acetate. The organic layer was washed with water (25 mL), brine (25 mL), dried over anhydrous sodium sulfate and concentrated under vacuum to afford the product as pale yellow colored solid. The product was further purified by recrystallization using pet ether/ether. (9.9 g, 72.2%)

Step F (2): To a suspension of NaH (1.37 g, 0.034 mol) in dry DMF (5 mL) under $N_2$, the compound of step F (1) (10 g, 0.034 mol) was added at 0° C. The reaction mixture was stirred for about 30 min. at room temperature. The reaction mixture was again cooled to 0° C. and bromoacetyl bromide (7.62 g, 0.037 mol) was added and allowed to stir overnight at room temperature. The reaction mixture was poured on to crushed ice and the precipitate was extracted with ethyl acetate (3×50 ml). The organic layer was washed with water (25 ml), brine (25 ml), dried over anhydrous sodium sulfate and concentrated under vacuum. The resulting product was purified by column chromatography using $CHCl_3$:MeOH (9:1) as eluent to afford the product as brown colored solid (6 g, 42.5%)

Step F (3): To a solution of the compound of step F (2) (6 g 0.014 mol) in dry DMF (60 ml) under $N_2$, anhydrous $K_2CO_3$ (6.03 g, 0.043 mol) was added with stirring. The reaction mixture was cooled to 0° C. and N,N-dimethylamine hydrochloride (2.37 g, 0.029 mol) was added at once. The reaction mixture was allowed stir for overnight at room temperature. The reaction mixture was poured into water and extracted with ethyl acetate (2×150 ml). The organic layer was washed with water (25 ml), brine (25 ml), dried over anhydrous sodium sulfate and concentrated under vacuum to remove the volatiles. The resulting crude product was purified by column chromatography using CHCl₃:MeOH (9:1) as eluent to afford the product as an off-white solid (4 g, 72.9%)

Step F (4): To a solution of the compound of step F (3) (12 g) in dry 1, 4-dioxane (50 ml), HCl in dioxane (100 ml) was added while stirring. The reaction mixture was heated to 50° C. over night. After ensuring the absence of the starting material, the reaction mixture was concentrated under vacuum to remove the dioxane and the obtained solid was washed with pet ether/ether mixture to provide the pure product as a white solid in its HCl salt form (9 g, 90.4%) ¹H NMR (400 MHz, (CD₃)₂SO): δ 11.05 (s, 1 H), 10.2 (br s, 1 H), 8.63 (br s, 2 H), 7.75 (s, 2 H), 4.24 (s, 2 H), 4.05 (s, 2 H), 2.87 (s, 6 H).

Intermediate G

N-(4-(Aminomethyl)-2-chloro-6-methylphenyl)-2-(dimethylamino)acetamide

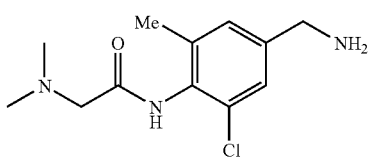

The title compound was prepared as outlined in the scheme following the general procedures for the preparation of Intermediate F.

LC/MS Method A: Column: XTERRA 4.6×30 mm S5; Flow Rate: 4 mL/min.; Solvent A: 10% MeOH-90% water-0.1% TFA; Solvent B: 90% MeOH-10% water-0.1% TFA; Gradient: % B 0-100; Gradient Time: 3 min.

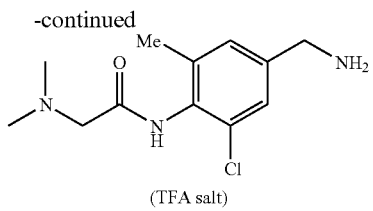

(TFA salt)

Step G (1): 4-(N-Boc-Aminomethyl)-2-chloro-6-methyl-benzenamine
¹H NMR (500 MHz, CDCl₃) δ 7.06 (s, 1 H), 6.88 (s, 1 H), 4.15 (s, 2 H), 2.18 (s, 3 H), 1.45 (s, 9 H); LC/MS RT (Method A)=2.841 min.; (M+H)⁺=271 (base peak 215).

Step G (2): N-(4-(N-Boc-Aminomethyl)-2-chloro-6-methylphenyl)-2-bromoacetamide
¹H NMR (500 MHz, CDCl₃) δ 7.87 (s, 1 H), 7.21 (s, 1 H), 7.07 (s, 1 H), 4.85 (s, 1 H), 4.25 (d, J=5.5 Hz, 2 H), 4.06 (s, 2 H), 2.25 (s, 3H), 1.46 (s, 9 H); LC/MS RT (Method A)=2.866 min.; (M+H)⁺=none (base peak 369.04).

Step G (3): N-(4-(N-Boc-Aminomethyl)-2-chloro-6-methylphenyl)-2-(dimethylamino)acetamide
¹H NMR (500 MHz, CDCl₃) δ 8.82 (s, 1 H), 7.18 (s, 1 H), 7.04 (s, 1 H), 4.91 (s, 1 H), 4.22 (d, J=5.5 Hz, 2 H), 3.12 (s, 2 H), 2.43 (s, 6 H), 2.24 (s, 3 H), 1.44 (s, 9 H); LC/MS RT (Method A)=2.330 min.; (M+H)⁺=356.2.

Step G (4): N-(4-(Aminomethyl)-2-chloro-6-methylphenyl)-2-(dimethylamino)-acetamide
The title compound was prepared from 4-(aminomethyl)-2-chloro-6-methylbenzenamine following the general procedures as described for the preparation of Intermediate F.
¹H NMR (500 MHz, CD₃OD) δ 7.48 (s, 1H), 7.35 (s, 1H), 4.28 (s, 2 H), 4.10 (s, 2 H), 3.01 (s, 6 H), 2.31 (s, 3 H); LC/MS (Method A) RT=0.193 min.; (M+H)⁺=256.

EXAMPLE 1

N-(2-(4-Acetamido-3,5-dichlorophenyl)-1-aminoethylidene)-3-(methoxyimino)-3-(4-methoxyphenyl)propanamide

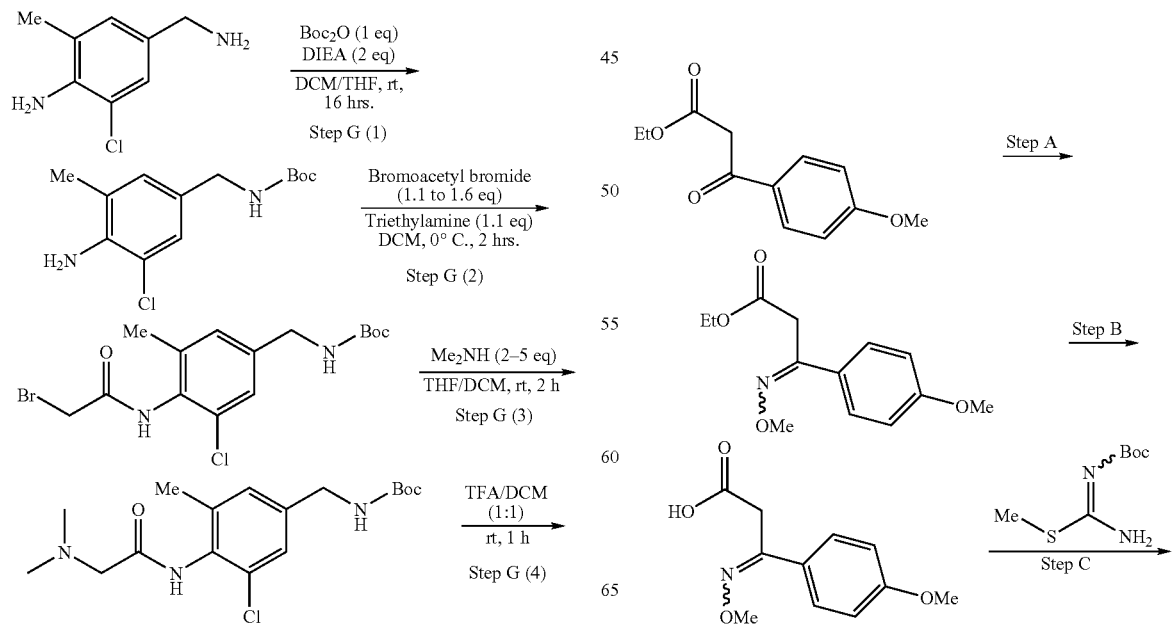

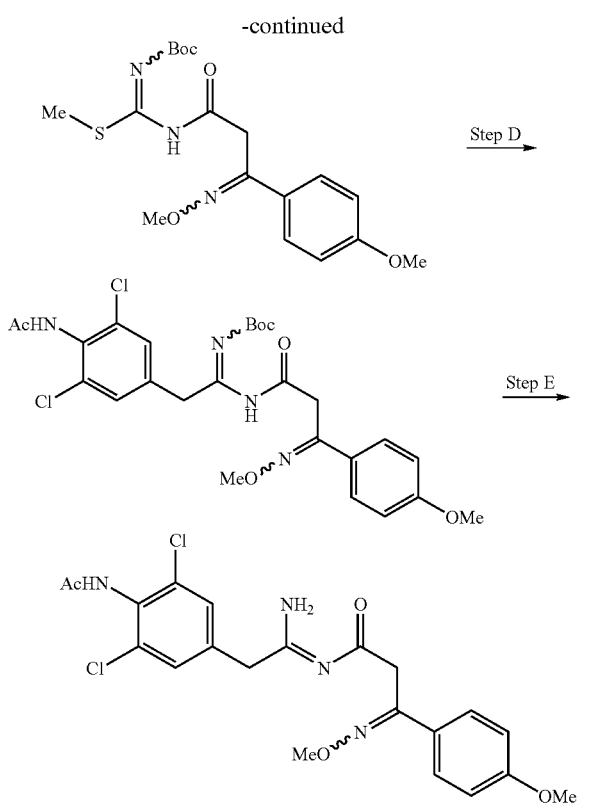

Step A: Ethyl 3-(methoxyimino)-3-(4-methoxyphenyl) propanoate

A mixture of ethyl 3-(4-methoxyphenyl)-3-oxopropanoate (500 mg) and MeONH$_2$.HCl (207 mg) in ethanol (4 mL) was heated at 80° C. for 2 h. Ethanol was removed in vacuo, and saturated sodium bicarbonate was added to the residue. The aqueous solution was extrated with ethyl acetate (x4), and the combined organic layers were washed with brine, dried over anhydrous sodium sulfate, and filtered. The filtrate was evaporated in vacuo to give the title compound as a colorless oil, which was used directly in the Step B. HPLC retention time: 2.02 min (method A). MS (ESI) (M+H)$^+$ 252.14.

Step B: 3-(Methoxyimino)-3-(4-methoxyphenyl)propanoic acid

To a solution of ethyl 3-(methoxyimino)-3-(4-methoxyphenyl)propanoate from Step A in THF (5 mL) was added 1 N lithium hydroxide (5 mL), and the resulting solution was stirred at room temperature for 12 h. Most of the solvents were removed in vacuo, and 1N hydrochloric acid (5 mL) was added. The aqueous layer was extrated with ethyl acetate (x4), and the combined organic layers were washed with brine, dried over anhydrous sodium sulfate, and filtered. The filtrate was evaporated in vacuo to give the title compound as a white solid (350 mg). $^1$H NMR (400 MHz, CDCl$_3$) δ 7.58 (m), 6.89 (m), 4.00 (s), 3.96 (3), 3.81 (s), and 3.78 (s).

Step C: tert-Butyl (3-(methoxyimino)-3-(4-methoxyphenyl)-propanamido)(methylthio)methylenecarbamate A mixture of 3-(methoxyimino)-3-(4-methoxyphenyl) propanoic acid (223 mg), tert-butyl amino(methylthio)methylenecarbamate (190 mg), EDAC.HCl (384 mg), DMAP (122 mg) and triethylamine (0.56 mL) in dichloromethane (3 mL) was stirred at room temperature for 12 h. The crude reaction mixture was purified directly by preparative TLC eluting with 35% ethyl acetate/75% hexanes to give the title compound as a yellowish oil (350 mg). HPLC retention time: 2.42 min (method A). MS (ESI) (M+Na)$^+$ 418.18.

Step D: tert-butyl 2-(4-acetamido-3,5-dichlorophenyl)-1-(3-(methoxyimino)-3-(4-methoxyphenyl)propanamido)ethylidenecarbamate A solution of tert-butyl (3-(methoxyimino)-3-(4-methoxyphenyl-propanamido)-(methylthio)methylenecarbamate (15 mg) and N-(4-(aminomethyl)-2,6-dichlorophenyl)acetamide (20 mg) in THF (0.15 mL) was stirred at room temperature for 12 h. The crude reaction mixture was purified directly by preparative TLC eluting with 35% ethyl acetate/75% hexanes to give the title compound as a yellowish oil (12 mg). $^1$H NMR (400 MHz, CDCl$_3$) δ 7.67 (d, J=8.80 Hz), 7.56 (d, J=9.20 Hz), 7.19 (s), 6.88 (d, J=8.80 Hz), 6.80 (d, J=8.80 Hz), 4.51 (br. D), 4.07 (s), 3.94 (s), 3.80 (s), 3.79 (s), 2.22 (s), 1.45 (s).

Step E: N-(2-(4-Acetamido-3,5-dichlorophenyl)-1-aminoethylidene)-3-(methoxyimino)-3-(4-methoxyphenyl)propanamide To a solution of tert-butyl 2-(4-acetamido-3,5-dichlorophenyl)-1-(3-(methoxyimino)-3-(4-methoxyphenyl)-propanamido)ethylidenecarbamate (12 mg) in dichloromethane (0.10 mL) was added TFA (0.10 mL), and the resulting mixture was stirred at room temperature for 12 h. The solvents were removed in vacuo to give the title compound as its TFA salt (10 mg). Retention time: 1.75 min (method A). MS (ESI) (M+H)$^+$ 482.19.

EXAMPLE 2

N-(1-Amino-2-(4-amino-3,5-dichlorophenyl)ethylidene)-3-(methoxyimino)-3-(4-methoxyphenyl) propanamide

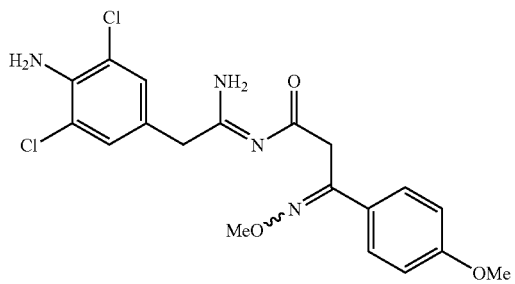

The title compound was prepared in the same manner as shown in the Example 1 with the exception that 4-(aminomethyl)-2,6-dichlorobenzenamine was used in Step D. Retention time: 1.90 min (method A). MS (ESI) (M+H)$^+$ 440.14.

EXAMPLE 3

N-(1-Amino-2-(3,5-dichlorophenyl)ethylidene)-3-(methoxyimino)-3-(4-methoxyphenyl)propanamide

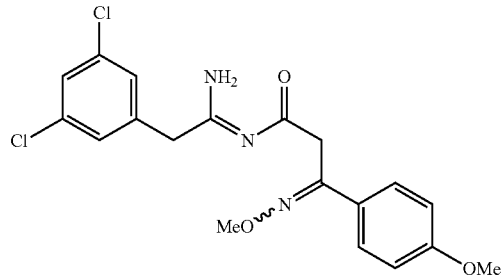

The title compound was prepared in the same manner as shown in the Example 1 with the exception that (3,5-dichlorophenyl)methanamine was used in Step D. retention time: 2.09 min (method A). MS (ESI) (M+H)+ 423.16.

EXAMPLE 4

N-(1-Amino-2-(3-chloro-4-(2-(dimethylamino)acetamido)-5-methylphenyl)-ethylidene)-3-(methoxyimino)-3-(4-methoxyphenyl)propanamide

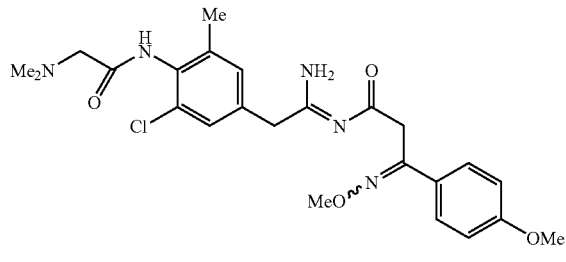

The title compound was prepared in the same manner as shown in the Example 1 with the exception that N-(4-(aminomethyl)-2-chloro-6-methylphenyl)-2-(dimethylamino)acetamide was used in Step D. Retention time: 1.39 min (method A). MS (ESI) (M+H)+ 503.05.

EXAMPLE 5

N-(2-(4-Acetamido-3,5-dichlorophenyl)-1-aminoethylidene)-3-(ethoxyimino)-3-(4-methoxyphenyl)propanamide

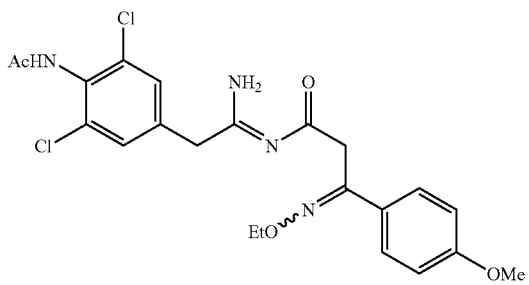

The title compound was prepared in a similar manner to that described in Example 1 with the exception that EtONH$_2$.HCl was used in Step A. Retention time: 1.65 min (method A). MS (ESI) (M+H)+ 493.95.

EXAMPLE 6

N-(1-Amino-2-(4-amino-3,5-dichlorophenyl)ethylidene)-3-(ethoxyimino)-3-(4-methoxyphenyl)propanamide

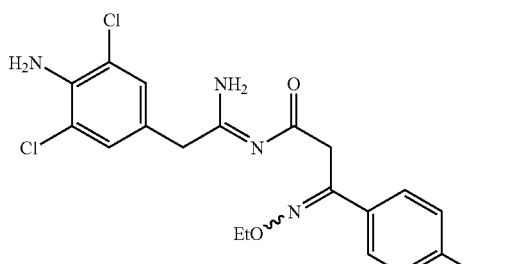

The title compound was prepared in a similar manner to that described in Example 2 with the exception that EtONH$_2$.HCl was used in Step A of Example 1. Retention time: 1.81 min (method A). MS (ESI) (M+H)+ 451.94.

EXAMPLE 7

N-(1-Amino-2-(3-chloro-4-(2-(dimethylamino)acetamido)-5-methylphenyl)-ethylidene)-3-(methoxyimino)-3-(4-methoxyphenyl)propanamide

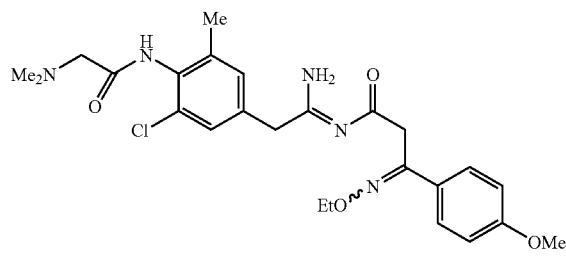

The title compound was prepared in a similar manner to that described in Example 4 with the exception that EtONH$_2$.HCl was used in Step A of Example 1. Retention time: 1.47 min (method A). MS (ESI) (M+H)+ 517.04.

EXAMPLE 8

N-(2-(4-Acetamidophenyl)-1-aminoethylidene)-3-(methoxyimino)-3-(4-methoxyphenyl)propanamide

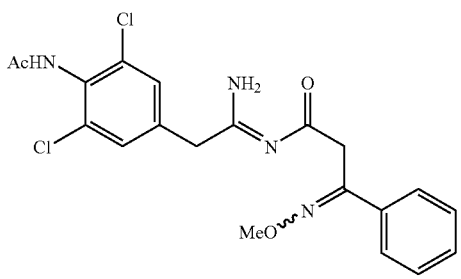

The title compound was prepared in a similar manner to that described in Example 1 with the exception that ethyl 3-oxo-3-phenylpropanoate was used in Step A. Retention time: 1.54 min (method A). MS (ESI) (M+H)+ 450.15.

EXAMPLE 9

N-(1-Amino-2-(4-amino-3,5-dichlorophenyl)ethylidene)-3-(methoxyimino)-3-phenylpropanamide

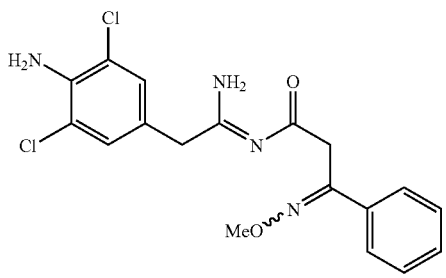

The title compound was prepared in a similar manner to that described in Example 1 with the exception that ethyl 3-oxo- 3-phenylpropanoate was used in Step A. Retention time: 1.74 min (method A). MS (ESI) (M+H)+ 408.13.

EXAMPLE 10

N-(1-Amino-2-(4-amino-3,5-dichlorophenyl)ethylidene)-3-(methoxyimino)-3-phenylpropanamide

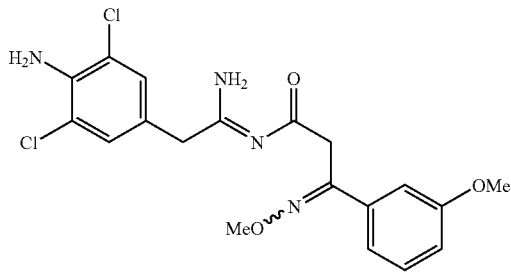

The title compound was prepared in a similar manner to that described in Example 1 with the exception that ethyl 3-(3-methoxyphenyl)-3-oxopropanoate was used in Step A. Retention time: 1.72 min (method A). MS (ESI) (M+H)+ 438.17.

EXAMPLE 11

N-(2-(4-Acetamido-3,5-dichlorophenyl)-1-aminoethylidene)-3-(methoxyimino)-3-(3-methoxyphenyl)propanamide

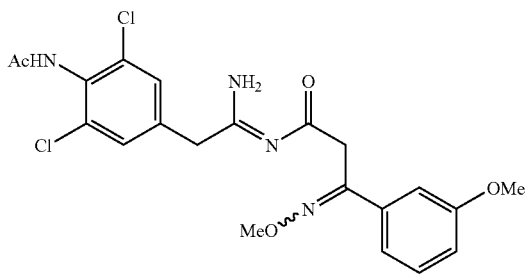

The title compound was prepared in a similar manner to that described in Example 1 with the exception that ethyl 3-(3-methoxyphenyl)-3-oxopropanoate was used in Step A. Retention time: 1.58 min (method A). MS (ESI) (M+H)+ 480.19.

EXAMPLE 12

N-(2-(4-Acetamido-3,5-dichlorophenyl)-1-aminoethylidene)-3-(methoxyimino)-3-(2-methoxyphenyl)propanamide

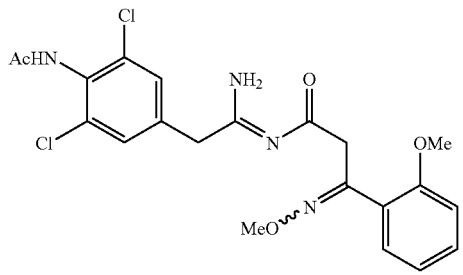

The title compound was prepared in a similar manner to that described in Example 1 with the exception that ethyl 3-(2-methoxyphenyl)-3-oxopropanoate was used in Step A. Retention time: 1.53 min (method A). MS (ESI) (M+H)+ 480.21.

EXAMPLE 13

N-(1-Amino-2-(4-amino-3,5-dichlorophenyl)ethylidene)-3-(methoxyimino)-3-(2-methoxyphenyl)propanamide

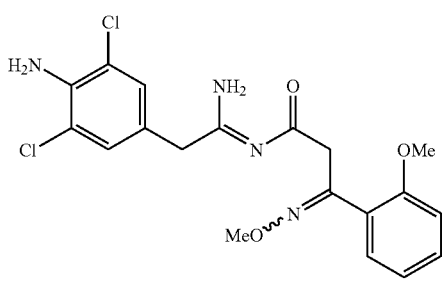

The title compound was prepared in a similar manner to that described in Example 1 with the exception that ethyl 3-(2-methoxyphenyl)-3-oxopropanoate was used in Step A. Retention time: 1.69 min (method A). MS (ESI) (M+H)+ 438.18.

EXAMPLE 14

N-(1-Amino-2-(4-amino-3,5-dichlorophenyl)ethylidene)-3-(4-fluorophenyl)-3-(methoxyimino)propanamide

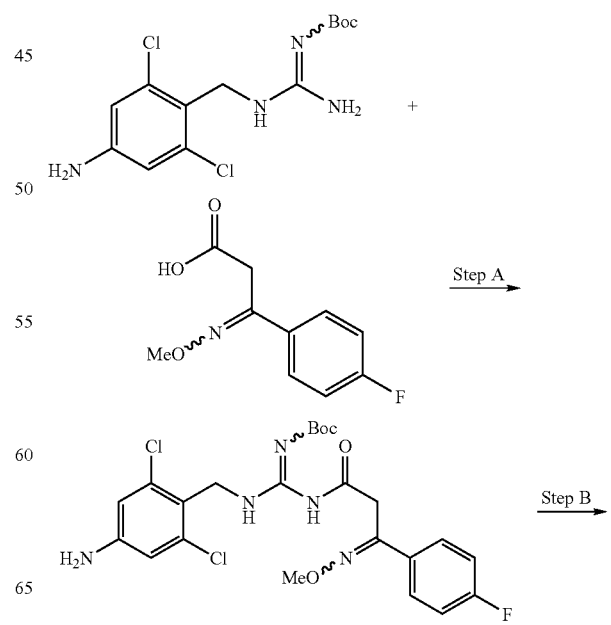

-continued

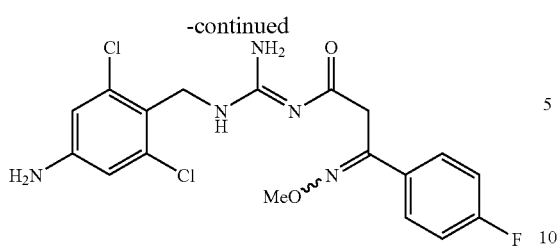

Step A: tert-Butyl (4-amino-3,5-dichlorophenylamino)(3-(4-fluorophenyl)-3-(methoxyimino)propanamido)methylenecarbamate A mixture of tert-butyl (4-amino-2,6-dichlorobenzylamino)(amino)-methylenecarbamate (11 mg), 3-(4-fluorophenyl)-3-(methoxyimino)propanoic acid (10 mg), PyBOP (20 mg) and triethylamine (15 µL) in dichloromethane (0.10 mL) was stirred at room temperature for 12 h. The crude product was purified by preparative TLC eluting with 50% ethyl acetate/50% hexanes to give the title compound as a colorless oil (9 mg). retention time: 2.41 min (method A). MS (ESI) (M+H)$^+$ 525.92.

Step B: N-(1-Amino-2-(4-amino-3,5-dichlorophenyl)ethylidene)-3-(4-fluorophenyl)-3-(methoxyimino)propanamide To a solution of tert-Butyl (4-amino-3,5-dichlorophenylamino)(3-(4-fluorophenyl)-3-(methoxyimino)-propanamido)methylenecarbamate (7 mg) in dichloromethane (0.10 mL) was added TFA (0.10 mL) and the resulting solution was stirred at room temperature for 12 h. The solvents were removed in vacuo to give the title compound as a sightly yellowish oil (6 mg). Retention time: 1.69 min (method A). MS (ESI) (M+H)$^+$ 425.84.

EXAMPLE 15

N-(2-(4-Acetamido-3,5-dichlorophenyl)-1-aminoethylidene)-3-(4-fluorophenyl)-3-(methoxyimino)propanamide

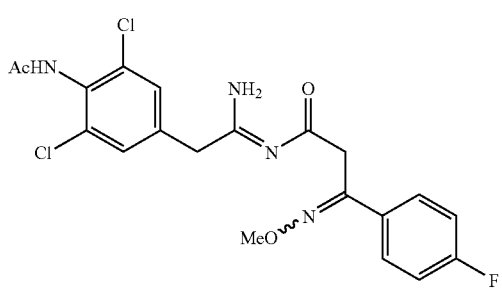

The title compound was prepared in a similar manner to that described in Example 14 with the exception that tert-butyl (4-acetamido-3,5-dichlorophenyl-amino)(amino)methylenecarbamate was used in Step A. retention time: 1.53 min (method A). MS (ESI) (M+H)$^+$ 467.86.

EXAMPLE 16

N-(2-(4-Acetamido-3,5-dichlorophenyl)-1-aminoethylidene)-3-(4-nitrophenyl)-3-(methoxyimino)propanamide

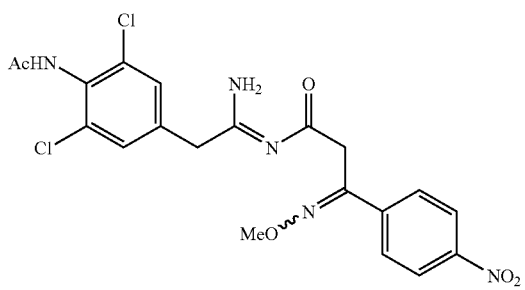

The title compound was prepared in a similar manner to that described in Example 14. Retention time: 1.54 min (method A). MS (ESI) (M+H)$^+$ 494.84.

EXAMPLE 17

N-(1-Amino-2-(4-amino-3,5-dichlorophenyl)ethylidene)-3-(methoxyimino)-3-(4-nitrophenyl)propanamide

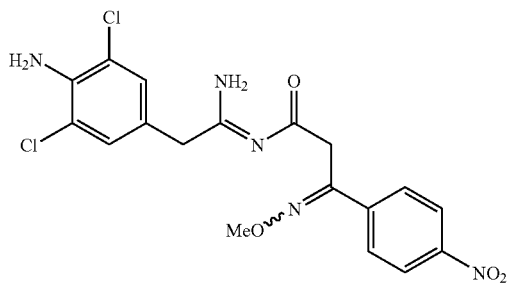

The title compound was prepared in a similar manner to that described in Example 14. Retention time: 1.70 min (method A). MS (ESI) (M+H)$^+$ 452.82.

EXAMPLE 18

N-((4-acetamido-3,5-dichlorobenzylamino)(amino)methylene)-3-(isobutoxyimino)-3-(4-methoxyphenyl)propanamide

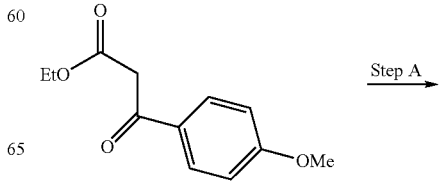

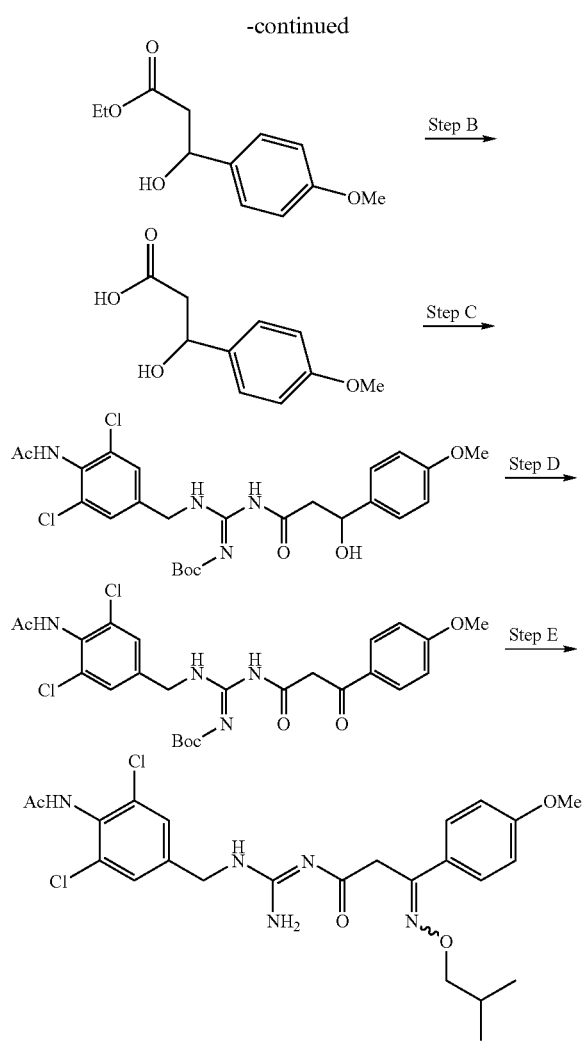

Step A: Ethyl 3-hydroxy-3-(4-methoxyphenyl)propanoate

A solution of ethyl 3-(4-methoxyphenyl)-3-oxopropanoate (444 mg, 2 mmol) in methanol (4 mL) was added sodium borohydride (76 mg, 2.0 mmol) at 0° C. slowly. After addition, the reaction mixture was stirred at 0° C. for 30 min. Two drops of saturated sodium sulfate solution were added to the reaction mixture to quench the reaction. Methanol was removed in vacuo, and water was added to the residue. The aqueous solution was extrated with ethyl acetate (x3), and the combined organic layers were dried over anhydrous sodium sulfate, and filtered. The filtrate was evaporated in vacuo. The crude mixture was purified by Flash Chromatography with eluent of 40% ethyl acetate/60% hexane to give the title compound as a clear oil (252 mg, 56% yield). $^1$H NMR (400 MHz, CDCl$_3$) δ 1.22-1.28 (m, 3 H) 2.63-2.75 (m, 2 H) 3.79 (s, 3 H) 4.16 (q, J=7.13 Hz, 2 H) 5.07 (dd, J=9.06, 3.78 Hz, 1 H) 6.85-6.89 (m, 2 H) 7.24-7.31 (m, 2 H). HPLC retention time: 1.973 min (method A). MS (ESI) (M+Na)$^+$ 246.96.

Step B: 3-Hydroxy-3-(4-methoxyphenyl)propanoic acid

To a solution of ethyl 3-hydroxy-3-(4-methoxyphenyl)propanoate (252 mg, 1.1 mmol) in THF (1.1 mL) was added 1 N lithium hydroxide (1.1 mL), and the resulting solution was stirred at room temperature for 3 h. Most of the solvents were removed in vacuo, and 1N hydrochloric acid (1.1 mL) was added. The aqueous layer was extrated with ethyl acetate (x3), and the combined organic layers were dried over anhydrous sodium sulfate and filtered. The filtrate was evaporated in vacuo to give the title compound as an off-white solid (200 mg, 91% yield). $^1$H NMR (400 MHz, CD$_3$OD) δ 2.57-2.63 (m, 1 H) 2.65-2.72 (m, 1 H) 3.29 (s, 8 H) 3.76 (s, 3 H) 4.82 (s, 9 H) 5.01 (dd, J=8.56, 5.29 Hz, 1 H) 6.86 (ddd, J=9.19, 2.77, 2.39 Hz, 2 H) 7.26-7.30 (m, 2 H). HPLC retention time: 1.392 min (method A). MS (ESI) (M+Na)$^+$ 218.92.

Step C: (E)-tert-butyl (4-acetamido-3,5-dichlorobenzylamino)(3-hydroxy-3-(4-methoxyphenyl)propanamido)methylenecarbamate A mixture of 3-hydroxy-3-(4-methoxyphenyl)propanoic acid (13.7 mg, 0.07 mmol), (Z)-tert-butyl (4-acetamido-3,5-dichlorobenzylamino)(amino)-methylenecarbamate (26.3 mg), PyBop (36.4 mg), and triethylamine (0.01 mL) in dichloromethane (0.35 mL) was stirred at room temperature for 12 h. The crude reaction mixture was purified directly by preparative TLC eluting with 30% ethyl acetate/70% hexanes to give the title compound as a clear sticky oil (30 mg, 77% yield). $^1$H NMR (400 MHz, CDCl$_3$) δ 1.48 (m, 9 H) 2.21 (s, 3 H) 2.70 (m, 2 H) 3.78 (m, 3 H) 4.55 (m, 2 H) 4.95 (m, 1 H) 6.80-7.00 (m, 3 H) 7.24-7.38 (m, 4 H), 9.10 (m, 1 H), 12.30 (m, 1 H). HPLC retention time: 2.493 min (method A). MS (ESI) (M+H)$^+$ 553.08.

Step D: (E)-tert-butyl (4-acetamido-3,5-dichlorobenzylamino)(3-(4-methoxyphenyl)-3-oxopropanamido)methylenecarbamate A mixture of (E)-tert-butyl (4-acetamido-3,5-dichlorobenzylamino)(3-hydroxy-3-(4-methoxyphenyl)propanamido)methylenecarbamate (26 mg) and MnO$_2$ in dichloromethane (0.10 mL) was stirred at 50° C. for 12 h. The crude mixture was filtered and concentrated under vacuum to give the title compound as a yellow sticky oil (17 mg, 66% yield). $^1$H NMR (400 MHz, CDCl$_3$) δ 1.43-1.51 (9H, m), 1.11 (3H, s), 3.76-3.90 (5H, m), 4.35-4.69 (2H, m), 6.75-7.25 (4H, m), 7.26-7.90 (3H, m), 8.70 (1H, brd s), 11.90 (1H, brd s). HPLC retention time: 2.775 min (method A). MS (ESI) (M+H)$^+$ 551.01.

Step E: (E)-N-((4-acetamido-3,5-dichlorobenzylamino)-(amino)methylene)-3-(isobutoxyimino)-3-(4-methoxyphenyl)propanamide A mixture of (E)-tert-butyl (4-acetamido-3,5-dichlorobenzylamino)(3-(4-methoxyphenyl)-3-oxopropanamido)methylenecarbamate (6 mg) and O-isobutylhydroxylamine hydrochloride (3 mg) in ethanol (0.1 mL) was heated at 80° C. for 2 h. Ethanol was removed in vacuo and the crude mixture was purified by reverse phase HPLC (30×100 mm PHENOMENEX-LUNA S10 column, 10-90% methanol/H$_2$O/0.1% TFA) to give the title compound as a clear sticky oil.

hu 1H NMR (400 MHz, CD$_3$OD) δ 0.90 (6H, d, J=6.4 Hz), 1.49 (1H, m), 2.22 (3H, s), 3.80 (3H, s), 3.95-3.97 (4H, m), 4.40 (2H, m), 6.89 (2H, m), 7.18-7.28 (2H m), 7.55 (2H, m). HPLC retention time: 2.50 min (method A). MS (ESI) (M+H)$^*$ 522.17.

EXAMPLE 19

N-((4-amino-3,5-dichlorobenzylamino)(amino)methylene)-3-(isobutoxyimino)-3-(4-methoxyphenyl)propanamide

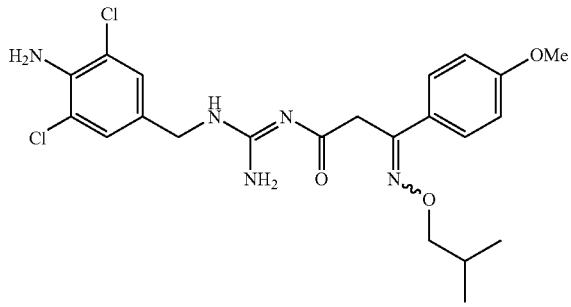

The title compound was prepared in the same manner as shown in the Example 14 with the exception that (Z)-tert-butyl (4-amino-3,5-dichlorobenzylamino)(amino)methylenecarbamate (Intermediate E) was used in Step A. $^1$H NMR (400 MHz, CD$_3$OD) δ 0.90 (6H, d, J=6.8 Hz), 2.00 (1H, m), 3.80 (3H, s), 3.94-3.97 (4H, m), 4.81 (2H, m), 6.89 (2H, m), 7.11 (2H, m), 7.52 (2H, m). HPLC retention time: 2.640 min (method A). MS (ESI) (M+H)$^+$480.00.

EXAMPLE 20

N-((4-amino-3,5-dichlorobenzylamino)(amino)methylene)-3-(1H-indol-3-yl)-3-(methoxyimino)propanamide

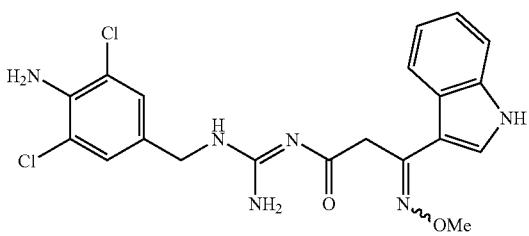

The title compound was prepared in a similar manner to that described in Example 1 with the exception that ethyl 3-(1H-indol-3-yl)-3-oxopropanoate was used in Step A. Retention time: 1.73 min (method A). MS (ESI) (M+H)$^+$ 447.07.

EXAMPLE 21

N-((4-acetamido-3,5-dichlorobenzylamino)(amino)methylene)-3-(1H-indol-3-yl)-3-(methoxyimino)propanamide

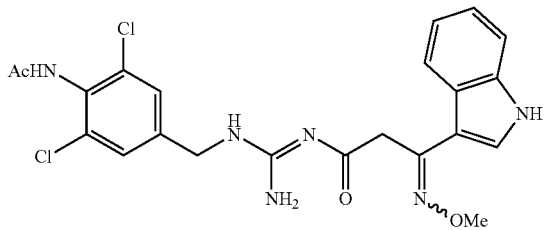

The title compound was prepared in a similar manner to that described in Example 1 with the exception that ethyl 3-(1H-indol-3-yl)-3-oxopropanoate was used in Step A. Retention time: 1.61 min (method A). MS (ESI) (M+H)$^+$ 489.09.

EXAMPLE 22

N-((3-chloro-4-(2-(dimethylamino)acetyl)-5-methylbenzylamino)(amino)-methylene)-3-(1H-indol-3-yl)-3-(methoxyimino)propanamide

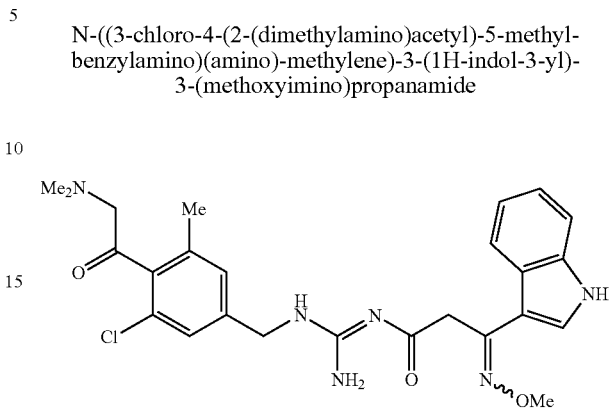

The title compound was prepared in a similar manner to that described in Example 1 with the exception that ethyl 3-(1H-indol-3-yl)-3-oxopropanoate was used in Step A. Retention time: 1.39 min (method A). MS (ESI) (M+H)$^+$ 512.20.

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in *Drosophila melanogaster* S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., (2001) "Characterization of recombinant, soluble beta-secretase from an insect cell expression system." *Mol. Pharmacol.* 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for C($^3$H)$_3$) were carried out using standard methods (Keen, M. (1999) in *Receptor Binding Techniques* (Walker, J. M. ed) p. 106 Humana Press, Totowa, N. J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 µg/ml penicillin, 10 µg/ml streptomycin, 3 µg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 µM, aprotinin 80 nM, leupeptin 2 µM, bestatin 4 µM, pepstatin A 1.5 µM, and E-64 1.4 µM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 µg/ml in assay buffer consisting of 50 mM HEPES pH 5.0 and 0.1% CHAPSO. Assays were initiated in polypropylene 96-well plates (Costar, Cambridge, Mass.) by the addition of 200 µl of cell homogenate to 50 µl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC50 values calculated using XLfit (IDBS, Guildford, UK).

Abbreviations:

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

Table 1

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

| Example # | Activity Rating[a] |
|---|---|
| 1 | +++ |
| 2 | ++ |
| 3 | + |
| 4 | ++ |
| 5 | +++ |
| 6 | ++ |
| 7 | ++ |

-continued

| Example # | Activity Rating[a] |
|---|---|
| 8 | +++ |
| 9 | ++ |
| 10 | ++ |
| 11 | ++ |
| 12 | ++ |
| 13 | + |
| 14 | ++ |
| 15 | +++ |
| 16 | +++ |
| 17 | ++ |
| 18 | ++ |
| 19 | + |
| 20 | ++ |
| 21 | +++ |
| 22 | ++ |

[a]Activity based on IC$_{50}$ values:
+++ = <0.1 µM
++ = 0.1–1.0 µM
+ = >1.0 µM In Vitro Assay to Identify β-Secretase Inhibitor Based on the Inhibition of Aβ Formation from Membrane Preparations An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA,* 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature,* 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but nontoxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, nontoxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, nontoxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I); or a stereoisomer thereof

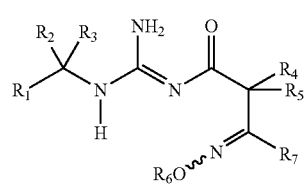

wherein $R_1$ is phenyl optionally substituted with one or more groups selected from halogen, CN, $CF_3$, OH, $-NH_2$, $C_{3-6}$cycloalkyl, $C_{1-6}$alkoxy, $C_{2-6}$alkenyl, $C_{1-6}$alkyl optionally substituted with OH or $-NH_2$, $-(CH_2)_m-NHC(=O)OC_{1-6}$ alkyl, $-(CH_2)_m-NHC(=O)O$phenyl optionally substituted with halogen; $-(CH_2)_m-NHC(=O)R_8$ and $-NHC(=O)R_9$;

$R_2$ and $R_3$ are each independently hydrogen, methyl or trifluoromethyl;

m is 0 or 1;

$R_4$ and $R_5$ are each independently hydrogen or fluoro;

$R_6$ is hydrogen, $C_{1-6}$alkyl, trifluoromethyl or $C_{3-6}$cycloalkyl;

$R_7$ is phenyl or indol-3-yl optionally substituted with one or more groups selected from halogen, CN, $CF_3$, $OCH_3$, $NO_2$, $NH_2$, and $NHC(=O)C_{1-6}$alkyl;

$R_8$ is $C_{1-6}$alkyl or $C_{3-6}$cycloalkyl in which each is optionally substituted with a group selected from halogen, CN, $CF_3$ and $C_{1-4}$alkoxy;

$R_9$ is $-C_{1-6}$alkylNR$_{10}$R$_{11}$;

$R_{10}$ is hydrogen or $C_{1-6}$alkyl;

$R_{11}$ is hydrogen, $C_{1-6}$alkyl optionally substituted with OH, halogen, $C_{1-4}$alkoxy or $C_{1-4}$alkylcarboxyl; $-(CH_2)_m C_{3-6}$cycloalkyl optionally substituted with phenyl or $C_{1-4}$alkyl; $-(CH_2)_m$phenyl optionally substituted with halogen, hydroxyl or $C_{1-4}$alkoxy; or $R_{10}$ and $R_{11}$ together with the nitrogen to which they are attached is azetidine, aziridine, pyrrolidine, piperidine or homopiperidine in which each is optionally substituted with a group selected from halogen, $C_{1-6}$alkyl and $C_{1-4}$alkoxy;

or a nontoxic pharmaceutically acceptable salt thereof.

2. The compound of claim 1, wherein $R_2$, $R_3$, $R_4$ and $R_5$ are hydrogen.

3. The compound of claim 2, wherein $R_6$ is methyl or ethyl.

4. The compound of claim 3, wherein $R_7$ is p-methoxyphenyl or indol-3-yl.

5. The compound of claim 4, wherein $R_1$ is 3,6-dichlophenyl, 4-amino-3,6-dichlorophenyl, 4-acetamido-3,5-dichlorophenyl or 4-acetamido-3-methyl-5-chlorophenyl.

6. The compound of claim 4 having the formula 1a, wherein $R_{10}$ is hydrogen or $C_{1-4}$alkyl; $R_{11}$ is hydrogen, $C_{1-4}$alkyl, trifluoromethyl or $C_{4-6}$cycloalkyl; or $R_{10}$ and $R_{11}$ together with the nitrogen to which they are attached is azetidine, aziridine, pyrrolidine, piperidine or homopiperidine; $R_{12}$ and $R_{13}$ are each independently selected from hydrogen, halogen, $C_{1-4}$alkyl and trifluoromethyl; or a nontoxic pharmaceutically acceptable salt thereof.

7. The compound according to claim 1 selected from the group consisting of:
- N-(2-(4-Acetamido-3,5-dichlorophenyl)-1-aminoethylidene)-3-(methoxyimino)-3-(4-methoxyphenyl)propanamide;
- N-(1-Amino-2-(4-amino-3,5-dichlorophenyl)ethylidene)-3-(methoxyimino)-3-(4-methoxyphenyl)propanamide;
- N-(1-Amino-2-(3,5-dichlorophenyl)ethylidene)-3-(methoxyimino)-3-(4-methoxyphenyl)propanamide;
- N-(1-Amino-2-(3-chloro-4-(2-(dimethylamino)acetamido)-5-methylphenyl)ethylidene)-3-(methoxyimino)-3-(4-methoxyphenyl)-propanamide;
- N-(2-(4-Acetamido-3,5-dichlorophenyl)-1-aminoethylidene)-3-(ethoxyimino)-3-(4-methoxyphenyl)propanamide;
- N-(1-Amino-2-(4-amino-3,5-dichlorophenyl)ethylidene)-3-(ethoxyimino)-3-(4-methoxyphenyl)propanamide;
- N-(1-Amino-2-(3-chloro-4-(2-(dimethylamino)acetamido)-5-methylphenyl)ethylidene)-3-(methoxyimino)-3-(4-methoxyphenyl)-propanamide;
- N-(2-(4-Acetamidophenyl)-1-amino ethylidene)-3-(methoxyimino)-3-(4-methoxyphenyl)propanamide;
- N-(1-Amino-2-(4-amino-3,5-dichlorophenyl)ethylidene)-3-(methoxyimino)-3-phenylpropanamide;
- N-(1-Amino-2-(4-amino-3,5-dichlorophenyl)ethylidene)-3-(methoxyimino)-3-phenylpropanamide;
- N-(2-(4-Acetamido-3,5-dichlorophenyl)-1-aminoethylidene)-3-(methoxyimino)-3-(3-methoxyphenyl)propanamide;
- N-(2-(4-Acetamido-3,5-dichlorophenyl)-1-aminoethylidene)-3-(methoxyimino)-3-(2-methoxyphenyl)propanamide;
- N-(1-Amino-2-(4-amino-3,5-dichlorophenyl)ethylidene)-3-(methoxyimino)-3-(2-methoxyphenyl)propanamide;
- N-(1-Amino-2-(4-amino-3,5-dichlorophenyl)ethylidene)-3-(4-fluorophenyl)-3-(methoxyimino)propanamide;
- N-(2-(4-Acetamido-3,5-dichlorophenyl)-1-amino ethylidene)-3-(4-fluorophenyl)-3-(methoxyimino)propanamide;
- N-(2-(4-Acetamido-3,5-dichlorophenyl)-1-aminoethylidene)-3-(4-nitrophenyl)-3-(methoxyimino)propanamide;
- N-(1-Amino-2-(4-amino-3,5-dichlorophenyl)ethylidene)-3-(methoxyimino)-3-(4-nitrophenyl)propanamide;
- N-((4-acetamido-3,5-dichlorobenzylamino)(amino)-methylene)-3-(isobutoxyimino)-3-(4-methoxyphenyl)propanamide;
- N-((4-amino-3,5-dichlorobenzylamino)(amino)methylene)-3-(isobutoxyimino)-3-(4-methoxyphenyl)propanamide;
- N-((4-amino-3,5-dichlorobenzylamino)(amino)methylene)-3-(1H-indol-3-yl)-3-(methoxyimino)propanamide;
- N-((4-acetamido-3,5-dichlorobenzylamino)(amino)methylene)-3-(1H-indol-3-yl)-3-(methoxyimino)propanamide; and
- N-((3-chloro-4-(2-(dimethylamino)acetyl)-5-methylbenzylamino)(amino)-methylene)-3-(1H-indol-3-yl)-3-(methoxyimino)propanamide;

or a nontoxic pharmaceutically acceptable salt thereof.

8. A pharmaceutical composition comprising a therapeutically effective amount of a compound of claim 1 in association with a pharmaceutically acceptable adjuvant, carrier or diluent.

9. A method for the treatment of Alzheimer's Disease, cerebral amyloid angiopathy and Down's Syndrome which comprises administering to a mammal in need thereof a therapeutically effective amount of a compound of claim 1.

* * * * *